United States Patent
Miyashita et al.

(10) Patent No.: US 9,883,930 B2
(45) Date of Patent: Feb. 6, 2018

(54) METHOD FOR USING PLASMA-TREATED LIQUID

(71) Applicant: Panasonic Intellectual Property Management Co., Ltd., Osaka (JP)

(72) Inventors: Mariko Miyashita, Hyogo (JP); Katsumi Imada, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/163,665

(22) Filed: May 24, 2016

(65) Prior Publication Data

US 2016/0346068 A1   Dec. 1, 2016

(30) Foreign Application Priority Data

May 29, 2015   (JP) .................................. 2015-110765

(51) Int. Cl.
*A61N 1/44* (2006.01)
*A61C 17/02* (2006.01)

(52) U.S. Cl.
CPC ................ *A61C 17/02* (2013.01); *A61N 1/44* (2013.01)

(58) Field of Classification Search
CPC .................................. A61C 17/02; A61N 1/44
See application file for complete search history.

(56) References Cited

U.S. PATENT DOCUMENTS

2013/0196286 A1*  8/2013  Rutberg ................. A61C 17/02
                                                           433/88

FOREIGN PATENT DOCUMENTS

| EP | 2072471 | 6/2009 |
|----|---------|--------|
| JP | 2007-508918 | 4/2007 |
| JP | 2009-255027 | 11/2009 |
| JP | 2010-051557 | 3/2010 |
| JP | 2015-003297 | 1/2015 |
| JP | 2015-080489 | 4/2015 |
| WO | 2005/012186 | 2/2005 |
| WO | 2012/008062 | 1/2012 |

* cited by examiner

*Primary Examiner* — Sean E Conley
(74) *Attorney, Agent, or Firm* — McDermott Will & Emery LLP

(57) ABSTRACT

A method comprises: bringing a plasma-treated liquid having an oxidizing power into contact with an object in an area; and mixing water and the plasma-treated liquid which remains in the area after the plasma-treated liquid is brought into contact with the object.

8 Claims, 4 Drawing Sheets

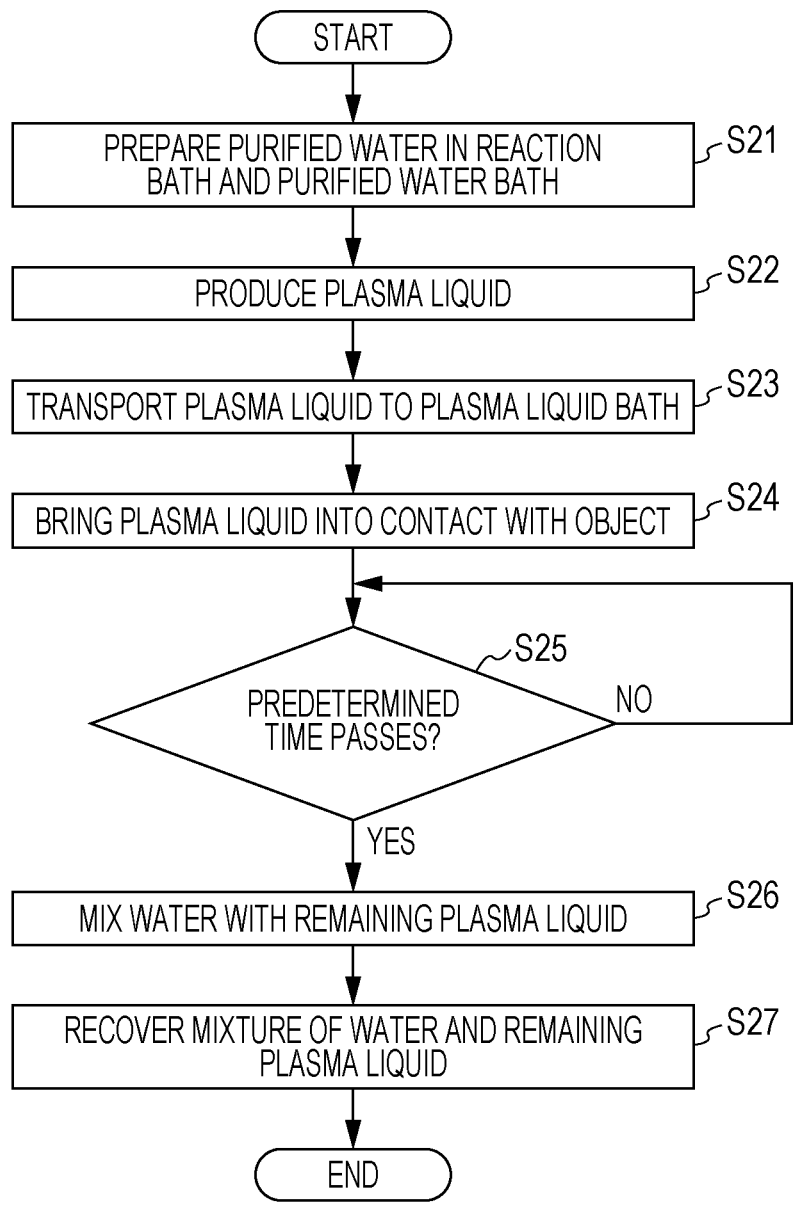

| GRAPH | CHANGE IN ABSORBANCE FROM 0 TO 30 SECONDS (%) |
|---|---|
| L0 | -9.51 |
| L1 | -0.964 |
| L2 | -1.91 |
| L3 | -0.396 |

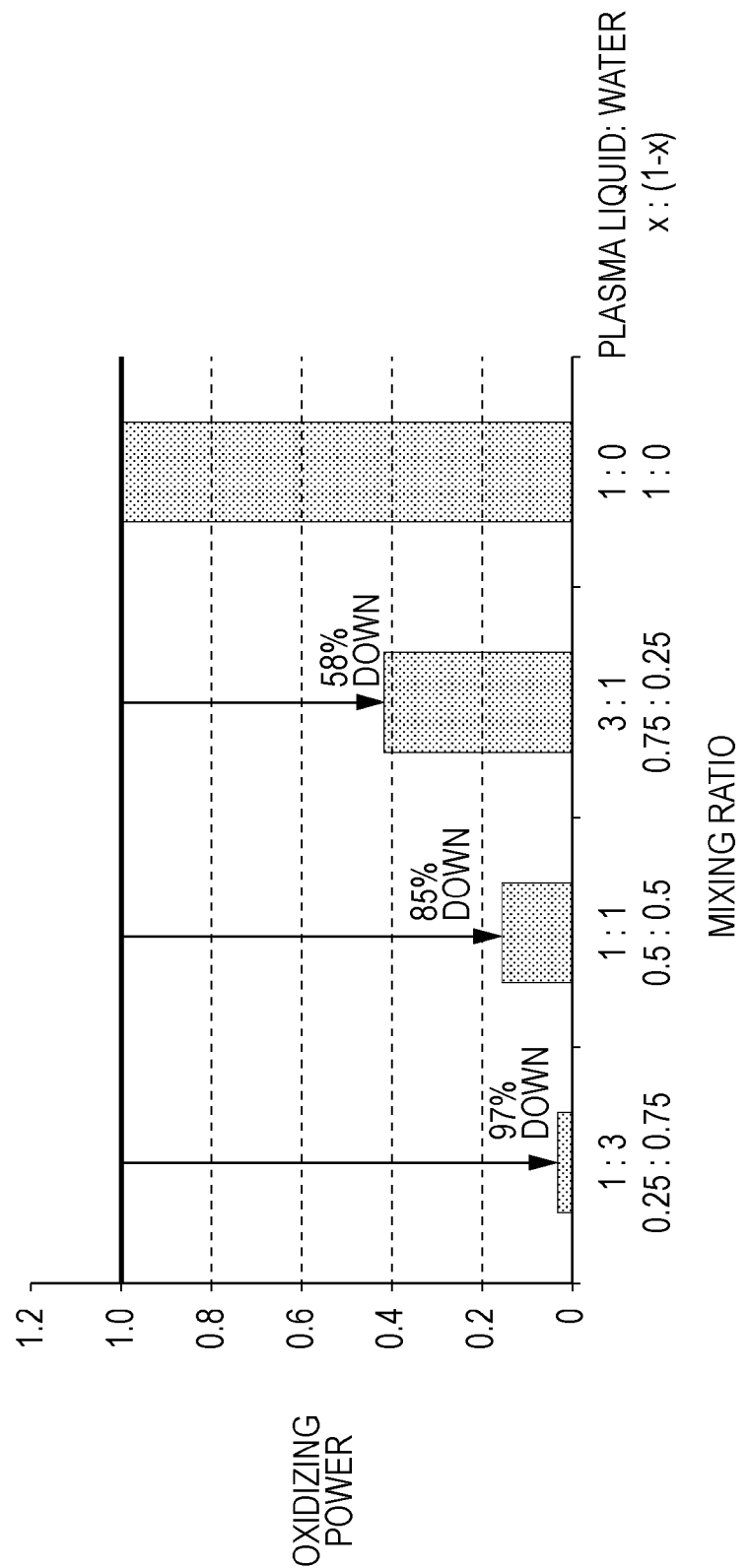

METHOD FOR USING PLASMA-TREATED LIQUID

BACKGROUND

1. Technical Field

The present disclosure relates to a method for using a plasma-treated liquid.

2. Description of the Related Art

Heretofore, a device and a method, each of which performs purification, sterilization, or the like of water using plasma, have been known. For example, Japanese Unexamined Patent Application Publication No. 2009-255027 has disclosed a device and a method for sterilizing microorganisms and bacteria by active species, such as hydrogen peroxide, generated using plasma.

SUMMARY

One non-limiting and exemplary embodiment provides a method for using a plasma-treated liquid.

In one general aspect, the techniques disclosed here feature a method comprising: bringing a plasma-treated liquid having an oxidizing power into contact with an object in an area; and mixing water and the plasma-treated liquid which remains in the area after the plasma-treated liquid is brought into contact with the object.

It should be noted that general or specific aspects of the present disclosure may be implemented using a device, a system, a method, an integrated circuit, a computer program, a computer-readable storage medium, or any selective combination thereof.

The method of the present disclosure is able to safely decrease an oxidizing power of a plasma-treated liquid.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 is a flowchart showing one example of a plasma liquid treatment method according to an embodiment;

FIG. 4 is a graph showing the relationship between an oxidizing power and a mixing ratio between a plasma liquid and water according to an embodiment.

Figure 1:
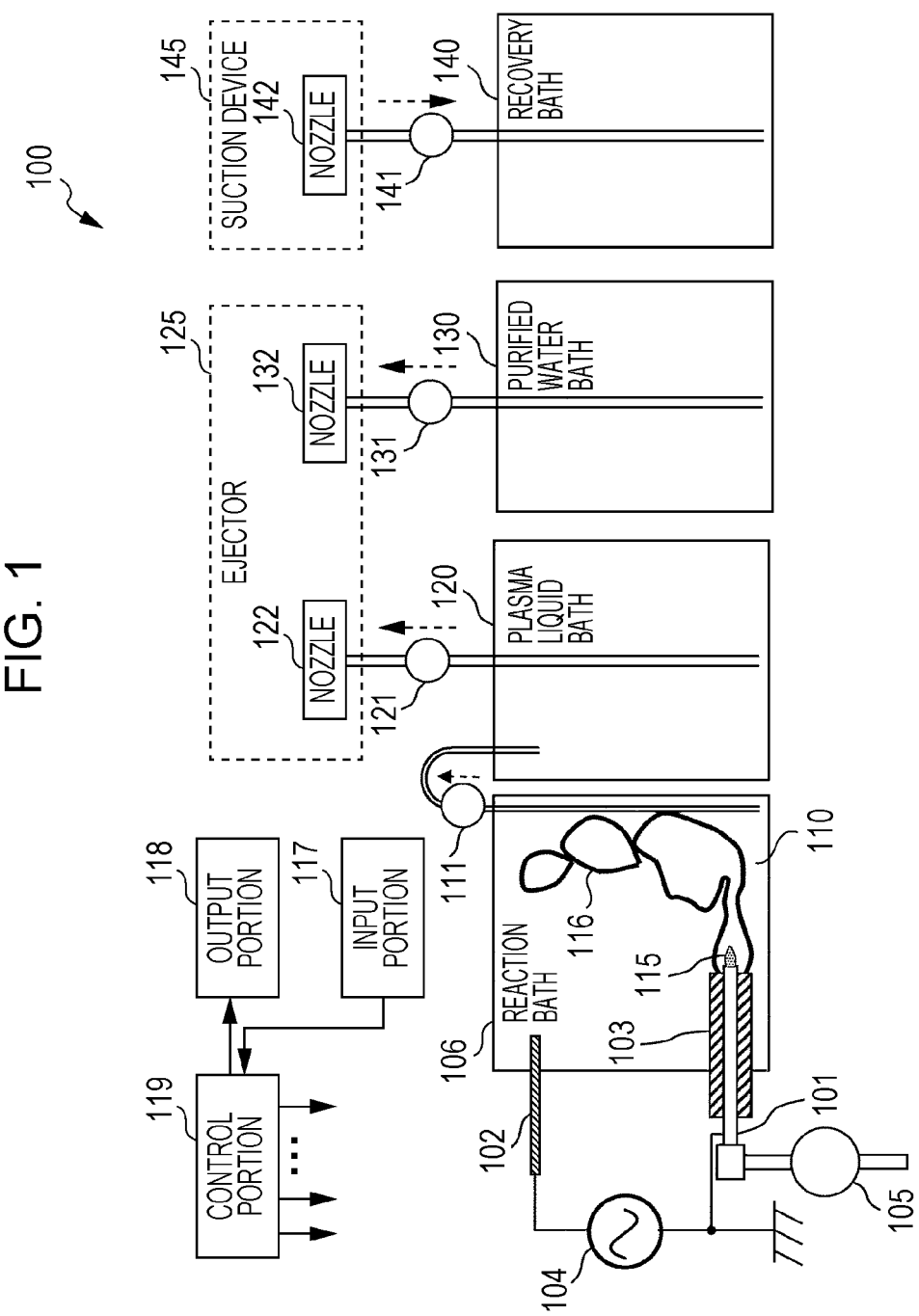
FIG. 1 is a block diagram showing a structural example of a plasma liquid treatment device according to an embodiment.

DETAILED DESCRIPTION (Finding Based on Present Disclosure)

The present inventors found that the plasma-treated liquid (hereinafter called as "plasma liquid") disclosed in the column of "Description of the Related Art" may cause the following problem.

For example, in purification of a liquid or a gas or sterilization of an object, as disclosed in Japanese Unexamined Patent Application Publication No. 2009-255027, a plasma generating device generates active species, such as OH radicals, by plasma, and microorganism and bacteria are sterilized by a strong oxidizing power of the active species. However, even after the treatment, such as sterilization, is finished, a strong oxidizing power may remain in the plasma liquid in many cases. Hence, in the case of application, such as oral cavity washing or bath room sterilization, in which a plasma liquid comes into contact with human bodies, damage may be done to skins and/or mucous membranes in some cases. In addition, when the plasma liquid is discarded without any appropriate treatments, the environment may be adversely influenced in some cases.

Through experimental research carried on the oxidizing power of a plasma liquid, the present inventors found the following point. That is, when a plasma liquid having an oxidizing power imparted by plasma is mixed with water, the oxidizing power can be significantly decreased as compared to that expected from the mixing ratio thereof.

Hence, a plasma liquid treatment method according to one aspect of the present disclosure comprises, in order to safely decrease the oxidizing power of a plasma liquid, bringing a plasma liquid formed by imparting an oxidizing power to a liquid by plasma with an object, and mixing water with a remaining plasma liquid which remains after the plasma liquid is brought into contact with the object.

According to the plasma liquid treatment method described above, since the object is sterilized by the plasma liquid, and furthermore, since the remaining plasma liquid is mixed with water, the oxidizing power of the remaining plasma liquid can be safely decreased.

In addition, according to a plasma liquid treatment device according to another aspect of the present disclosure, a plasma liquid formed by imparting an oxidizing power to a liquid by plasma is brought into contact with an object, and water is mixed with a remaining plasma liquid which remains after the plasma liquid is brought into contact with the object.

According to the plasma liquid treatment device described above, since the object is sterilized by the plasma liquid, and furthermore, since the remaining plasma liquid is mixed with water, the oxidizing power of the remaining plasma liquid can be safely decreased.

In addition, the plasma liquid treatment device described above may include an ejector which selectively ejects the plasma liquid or water to the object and a control portion which controls so that after the ejector ejects the plasma liquid, by ejection of the water from the ejector, the remaining plasma liquid and the water are mixed with each other.

According to the above plasma liquid treatment device, the oxidizing power of the remaining plasma liquid can be safely decreased, and furthermore, the object to be sterilized is not required to be immersed in the plasma liquid, and as a result, the range of objects to be treated can be significantly increased.

In addition, the plasma liquid treatment device may further include an input portion which receives a user operation, and after the ejector ejects the plasma liquid, the control portion may control the ejector so as to eject the water in accordance with the user operation received by the input portion.

Accordingly, the oxidizing power of the remaining plasma liquid can be safely decreased in accordance with the user operation.

In addition, the control portion may control the ejector so as to eject the water after a predetermined time passes from the start of the ejection of the plasma liquid by the ejector.

Accordingly, after a sufficient sterilization function is secured, the oxidizing power of the remaining plasma liquid can be safely decreased.

In addition, an oral cavity washing device according to another aspect of the present disclosure comprises the plasma liquid treatment device described above.

In addition, those general or specific aspects may be implemented using a device, a system, a method, an integrated circuit, a computer program, or a computer-readable storage medium, such as a CD-ROM, or may be implemented using any selective combination of a device, a system, a method, an integrated circuit, a computer program, and a storage medium.

Hereinafter, embodiments will be described in particular with reference to the drawings.

In addition, the following embodiments each show a general or a specific example. The numerical value, the shape, the material, the constituent element, the arrangement position and connection mode thereof, the steps, the order of the steps, and the like are each merely shown as one example and are not intended to limit the scope of the present disclosure. In addition, among the constituent elements of the following embodiments, a constituent element which is not described in the independent claim showing the top concept will be described as an arbitrary constituent element.

EMBODIMENTS

[1. Structural Example of Liquid Treatment Device]

FIG. 1 is a block diagram showing the structure of a plasma liquid treatment device 100 according to an embodiment. This plasma liquid treatment device 100 shows a structural example of an oral cavity washing device which is one type of nursing care device. As shown in FIG. 1, the plasma liquid treatment device 100 includes a first metal electrode 101, a second metal electrode 102, an insulating body 103, an electric source 104, a supply pump 105, a reaction bath 106, a pump 111, an input portion 117, an output portion 118, a control portion 119, a plasma liquid bath 120, a pump 121, an ejector 125, a purified water bath 130, a pump 131, a recovery bath 140, a pump 141, and a suction device 145. The ejector 125 includes a nozzle 122 and a nozzle 132. The suction device 145 includes a nozzle 142.

The ejector 125 may include the pumps 121 and 131. The ejector 125 is controlled by the control portion 119 as described below and selectively ejects a plasma liquid (plasma-treated liquid) or water to an object in an area (e.g. an oral cavity). For example, the control portion 119 controls the pumps 121 and 131 to control ejection operations of the ejector 125. The suction device 145 may include the pump 141. The control portion 119 may control the pump 141 to control suction operations of the suction device 145.

The first metal electrode 101 is, for example, a bar-like electrode and is arranged in the reaction bath 106 receiving a liquid 110 to be treated, that is, a liquid to be sterilized, so as to be at least partially exposed to the inside of the bath.

The second metal electrode 102 is, for example, a bar-like electrode and is arranged in the reaction bath 106 so as to be at least partially exposed to the inside of the bath.

The insulating body 103 is formed along the outer circumference of the first metal electrode 101 so as to provide an aeration space and is fitted to an opening of the reaction bath 106.

The electric source 104 generates plasma 115 by applying a voltage between the pair of electrodes, that is, between the first metal electrode 101 and the second metal electrode 102, and generates active species, such as OH radicals, in the liquid 110 to be sterilized.

The supply pump 105 supplies a gas into the space between the first metal electrode 101 and the insulating body 103. Accordingly, air bubbles 116 are continuously generated at a front end portion of the insulating body 103 and the first metal electrode 101. Although the plasma 115 is generated between the pair of electrodes without those air bubbles 116, by the presence of the air bubbles 116, the generation efficiency of active species caused by the plasma 115 can be increased.

The reaction bath 106 first stores purified water as the liquid 110 to be treated. The purified water is a raw liquid to be formed into a plasma liquid. Then, the reaction bath 106 stores a plasma liquid after the plasma 115 is generated. The plasma liquid is formed by imparting an oxidizing power to the liquid 110 to be treated by the plasma 115. This plasma liquid is transported to the plasma liquid bath 120 through a pipe of the pump 111. In addition, the reaction bath 106 and the plasma liquid bath 120 may be connected to each other using a pipe so that when the plasma 115 is generated, water (to be formed into the plasma liquid) is circulated between the reaction bath 106 and the plasma liquid bath 120.

The input portion 117 is an operation panel receiving a user (such as a care taker) operation. The input portion 117 includes, for example, an input circuit receiving a user operation. The user operation includes a start or a stop instruction of plasma discharge, an instruction of transporting a plasma liquid from the reaction bath 106 to the plasma liquid bath 120, a start or a stop instruction of ejection of a plasma liquid from the ejector 125, a start or a stop instruction of ejection of purified water from the ejector 125, a start or a stop instruction of suction by the suction device 145, and the like.

The output portion 118 is an LED, a display device, such as a liquid crystal panel, or an audio guidance device and outputs an operation condition of the plasma liquid treatment device 100 functioning as an oral cavity washing device, a progress status, an audio guidance, and the like.

The control portion 119 control the entire plasma liquid treatment device 100. The control portion 119 includes, for example, a control circuit controlling the entire plasma liquid treatment device 100. For example, the control portion 119 controls so that by ejection of the plasma liquid from the plasma liquid bath 120 through the nozzle 122, the plasma liquid is brought into contact with the object. Subsequently, the control portion 119 controls so that by ejection of the water from the purified water bath 130 through the nozzle 132, the water is mixed with the remaining plasma liquid.

The plasma liquid bath 120 stores the plasma liquid transported from the reaction bath 106.

The nozzle 122 is connected to a flexible pipe communicating with the plasma liquid bath 120, sucks the plasma liquid from the plasma liquid bath 120 by the pump 121 provided on the pipe, and ejects the plasma liquid. The nozzle 122 can be held in any way as a user wants. That is, the position and the ejection direction of the nozzle 122 can be freely determined. Accordingly, the ejection direction of the plasma liquid can be easily directed to the object. The ejection of the plasma liquid by the nozzle 122 can be used not only for general sterilization but also for sterilization of bacterial structural bodies called biofilms. The biofilm is formed of bacteria and an extrabacterial matrix (such as polysaccharides and/or DNA fragments) and is a structural body tougher than colonies. Since cells themselves are changed in a biofilm, sterilization may not be easily performed by a general sterilization operation in some cases. The plasma liquid can be produced from water as a raw material without using a special chemical reagent and has a high oxidizing power. Hence, the plasma liquid can be suitably used for sterilization of biofilms. In addition, the nozzle 122 may eject the plasma liquid either in the form of a mist or a liquid. In addition, the pump 121 may be either an electric pump or a manual pump such as a hand spray.

The purified water bath 130 stores water. This water may be either purified water or a liquid having a weak oxidizing power as compared to that of the plasma liquid.

The nozzle 132 is connected to a flexible pipe communicating with the purified water bath 130, sucks water from the purified water bath 130 by the pump 131 provided on the pipe, and ejects the water. The nozzle 132 can be held in any way as a user wants. That is, the position and the ejection direction of the nozzle 132 can be freely determined. For example, the nozzles 122 and 132 include universal joints or ball joints for this purpose. Accordingly, the ejection direction of water can be easily directed to the object. Since the remaining plasma liquid which remains after the plasma liquid is brought into contact with the object is mixed with water, the oxidizing power of the remaining plasma liquid can be decreased. That is, when water or water having an increased reducing power is simply mixed with the remaining plasma liquid, the oxidizing power can be easily and safely decreased. The details of the decrease in oxidizing power of the plasma liquid by mixing with water will be described later. In addition, the nozzle 132 may eject water either in the form of a mist or a liquid. In addition, the pump 131 may be either an electric pump or a manual pump such as a hand spray.

The recovery bath 140 is a tank recovering a mixed liquid of the remaining plasma liquid and the water.

The nozzle 142 sucks the mixed liquid of the plasma liquid and the water ejected from the ejector 125 and discharges the mixed liquid to the recovery bath 140. For example, in oral cavity washing, after the plasma liquid is ejected, water can be ejected, and furthermore, the mixed liquid can also be recovered. In addition, the pump 141 may be either an electric pump or a manual pump.

[2. Example of Operation of Plasma Liquid Treatment Device]

As for the plasma liquid treatment device 100 formed as described above, the operations thereof relating to sterilization, decrease in oxidizing power, and recovery will be described.

FIG. 2 is a flowchart showing one example of a plasma liquid treatment method according to this embodiment. By the control of the control portion 119, the treatment shown in FIG. 2 is performed along a user operation input to the input portion 117 together with a display or an audio guidance at the output portion 118.

In the flowchart shown in FIG. 2, first, water (such as purified water or water having a weak oxidizing power) is prepared as a raw liquid in the reaction bath 106 and the purified water bath 130 (S21). Subsequently, when the input portion 117 receives a user operation (such as a care taker's operation) indicating the completion of water preparation or a user operation instructing the start of plasma discharge, the control portion 119 controls so that a plasma liquid is produced from the water in the reaction bath 106 (S22). That is, the control portion 119 controls so that the plasma 115 is generated by applying a high voltage pulse from the electric source 104 between the first metal electrode 101 and the second metal electrode 102 to generate active species in the liquid. Accordingly, a plasma liquid having a high oxidizing power is produced.

Next, by the instruction of the control portion 119, the plasma liquid is transported from the reaction bath 106 to the plasma liquid bath 120 by the function of the pump 111 (S23), and furthermore, the plasma liquid is brought into contact with the object (S24). In the case of oral cavity washing, a care taker sprays the plasma liquid through the nozzle 122 to a portion to be sterilized in an oral cavity of a care receiver, so that the plasma liquid is brought into contact with the object. The object is a portion to be sterilized and for example, may be a portion in an oral cavity on which biofilms are present. When a predetermined time does not pass after the plasma liquid is brought into contact with the object, the contact state thereof is maintained (NO at S25). After this predetermined time passes, a sufficient sterilization function can be secured.

Furthermore, after the predetermined time passes (YES at S26), water is mixed with the remaining plasma liquid (S26). The remaining plasma liquid is a liquid which remains after the plasma liquid comes into contact with the object for a predetermined time and is a liquid in which active species still remain. In the case of oral cavity washing, water is sprayed from the nozzle 132 to the portion to be sterilized in the oral cavity. By this spray, the oxidizing power of the remaining plasma liquid can be safely decreased. In addition, the water used in this case may be any one selected from purified water, tap water, and hydrogen water and may be any water as long as having an oxidizing power weaker than that of the plasma liquid.

Next, a mixed liquid of the remaining plasma liquid and the water is sucked by the nozzle 142 and is recovered in the recovery bath 140 (S27). In particular, a care taker recovers a mixed liquid remaining in an oral cavity of a care receiver in the recovery bath 140 using the suction device 145 (that is, the nozzle 142). In addition, Steps other than Steps S24 and S26 may be arbitrarily omitted or modified.

[3. Experimental Data]

Next, the decrease in oxidizing power by mixing of the plasma liquid and the water will be described with reference to experimental data.

Figures 3A, 3B:
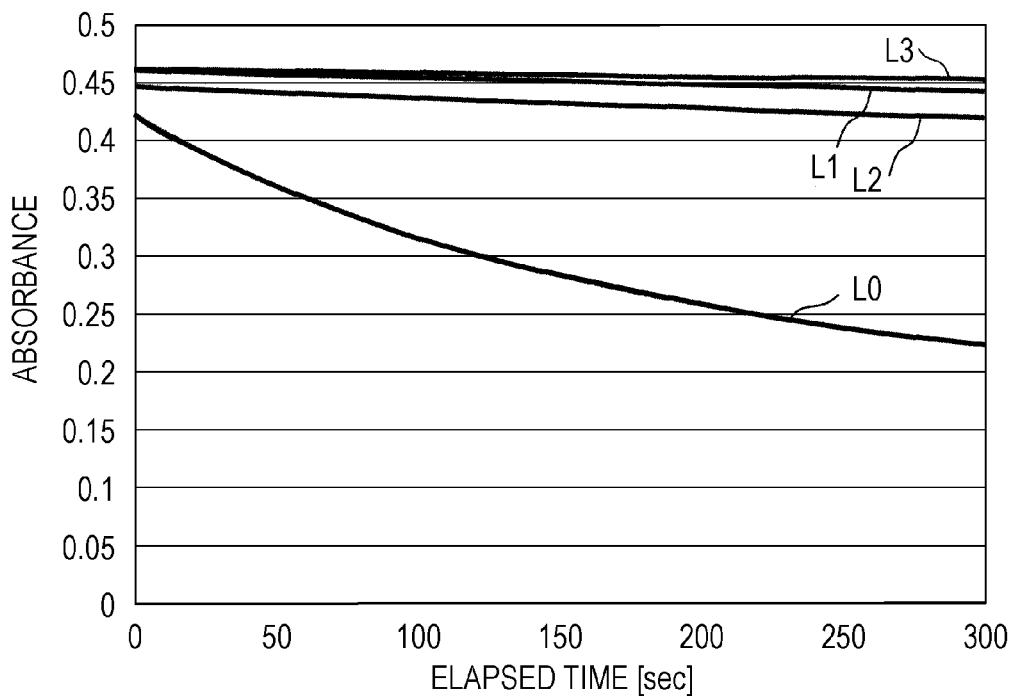
FIG. 3A is a graph showing the absorbance of a plasma liquid with an elapsed time according to an embodiment.
FIG. 3B is a view showing the change in absorbance of the plasma liquid after 30 seconds from the start of ejection thereof according to the embodiment.

FIG. 3A is a graph showing the absorbance of the plasma liquid with an elapsed time according to an embodiment. The horizontal axis of FIG. 3A represents the time (seconds). The vertical axis represents the absorbance. The change in absorbance is caused by the decomposition of Indigo carmine, which is a typical blue food coloring dye. That is, the decomposition of bacteria is regarded as the decomposition of dye. The lower side (small value side) of the vertical axis indicates that the decomposition of dye is advanced, that is, indicates that the oxidizing power of the plasma liquid is high. In addition, FIG. 3B shows the change in absorbance for 30 seconds from 0 to 30 seconds shown in FIG. 3A.

A graph L0 shows the change in absorbance of a plasma liquid itself produced so that the oxidizing power is maximized. In this experiment, indigo carmine is added in the liquid when the elapsed time is 0. According to the graph L0, the absorbance is rapidly decreased with the elapsed time. The reason for this is that the dye is rapidly decomposed by the oxidizing power of the plasma liquid. As shown in FIG.

3B, according to the graph L0, the change in absorbance for 30 seconds from 0 to 30 seconds is −9.51%.

A graph L1 shows the change in absorbance of a liquid obtained by mixing a plasma liquid produced so that the oxidizing power is maximized and an Indigo carmine aqueous solution in the same volume as that of the plasma liquid. Unlike the absorbance of the graph L0, the absorbance of the graph L1 is hardly changed. That is, the decomposition of the dye is not so much advanced. The reason for this is believed that the oxidizing power of the mixed liquid is decreased. As shown in FIG. 3B, the change in absorbance for 30 seconds is only −0.964%.

A graph L2 shows the change in absorbance of a liquid obtained by mixing a plasma liquid produced so that the oxidizing power is maximized and purified water in the same volume as that of the plasma liquid. In this experiment, indigo carmine is added in the liquid when the elapsed time is 0. Unlike the absorbance of the graph L0, the absorbance of the graph L2 is hardly changed. That is, the decomposition of the dye is not so much advanced. The reason for this is believed that the oxidizing power of the mixed liquid is decreased. As shown in FIG. 3B, the change in absorbance for 30 seconds is only −1.91%.

A graph L3 shows the change in absorbance of a liquid obtained by mixing a plasma liquid produced so that the oxidizing power is maximized and hydrogen water in the same volume as that of the plasma liquid. The hydrogen water is water in which hydrogen is dissolved and is believed to have an anti-oxidizing function. In this experiment, indigo carmine is added in the liquid when the elapsed time is 0. Unlike the absorbance of the graph L0, the absorbance of the graph L3 is hardly changed. That is, the decomposition of the dye is not so much advanced. The reason for this is believed that the oxidizing power of the mixed liquid is decreased. As shown in FIG. 3B, the change in absorbance for 30 seconds is only −0.396%. Although it is considered that the oxidizing power of the plasma liquid is significantly decreased due to the anti-oxidizing function of the hydrogen water, significant difference among the graphs L1, L2, and L3 is not actually observed.

As described above, from FIG. 3A, it is found that when the Indigo carmine aqueous solution, the purified water, and the hydrogen water are each mixed with the plasma liquid in the same volume as that thereof, the oxidizing power of the plasma liquid is significantly decreased. In addition, the function of decreasing the oxidizing power of the plasma liquid is not so much different among the Indigo carmine aqueous solution, the purified water, and the hydrogen water.

Next, experimental results on the relationship between the decrease in oxidizing power and the mixing ratio of the plasma liquid and water will be described.

FIG. 4 is a graph showing the relationship between the oxidizing power and the mixing ratio between the plasma liquid and water according to an embodiment. The horizontal axis of the graph shown in FIG. 4 represents the mixing ratio of the plasma liquid and water. In FIG. 4, as the mixing ratio (volume ratio in this case) of the plasma liquid and water, four ratios of 1:3, 1:1, 3:1, and 1:0 are shown. The vertical axis represents the oxidizing power of a mixed liquid between the plasma liquid and water, and the oxidizing power is normalized assuming that the oxidizing power of a plasma liquid having a mixing ratio of 1:0, that is, the oxidizing power of a plasma liquid containing no water, was regarded as 1. In addition, FIG. 4 shows the oxidizing power obtained 30 seconds after the water is mixed with the plasma liquid.

In the case of a mixing ratio of 3:1, that is, in the case in which the ratio of the water to the plasma liquid is 1:3, the decrease in oxidizing power is 58%. It is found that in order to decrease the oxidizing power of the plasma liquid to one half, water in an amount of one third of that of the plasma liquid may be mixed therewith.

In the case of a mixing ratio of 1:1, that is, in the case in which the ratio of the water to the plasma liquid is 1:1, the decrease in oxidizing power is 85%.

In the case of a mixing ratio of 1:3, that is, in the case in which the ratio of the water to the plasma liquid is 3:1, the decrease in oxidizing power is 97%.

As described above, it is found that the decrease in oxidizing power by mixing the water with the plasma liquid is not caused by a simple dilution effect, and the decrease in oxidizing power is significantly larger than the mixing ratio of the water.

In addition, from FIG. 4, it is found that the oxidizing power of the plasma liquid can be controlled by the mixing ratio of the water.

For example, when the amount of water to be mixed with the plasma liquid is ⅓ to 1 time the amount of the plasma liquid, the oxidizing power of the plasma liquid can be decreased by approximately 60% to 85%.

In addition, when the amount of water to be mixed with the plasma liquid is 1 to 3 times the amount of the plasma liquid, the oxidizing power of the plasma liquid can be decreased by approximately 85% to 97%.

In addition, when the amount of water to be mixed with the plasma liquid is 3 times or more the amount of the plasma liquid, the oxidizing power of the plasma liquid can be decreased by approximately 97% or more.

In addition, the amount of active species which remain in the remaining plasma liquid is actually depend on the amount of active species present in a plasma liquid which is not yet brought into contact with the object and on the concentration of the object with which the plasma liquid is to be brought into contact. Hence, the amount of water which can sufficiently decrease the oxidizing power of the remaining plasma liquid by mixing therewith is also depend on the two factors described above. Accordingly, for example, when the object is bacteria, before the plasma liquid is brought into contact with bacteria, the amount thereof may be detected, for example, by an image sensor or may be determined by visual inspection. When the amount of bacteria is large, since the amount of active species which remain after the contact is small, a small amount of water may be mixed with the remaining plasma liquid. On the other hand, when the amount of bacteria is small, since the amount of active species which remain after the contact is large, a large amount of water may be mixed with the remaining plasma liquid. Whether the amount of bacteria detected by a sensor is large or small may be determined by an arithmetic circuit based on a predetermined threshold. After the predetermined threshold is determined in consideration of the amount of a raw liquid of a plasma liquid to be stored in the reaction bath 106 and the amount of active species to be produced when the voltage applied between the electrodes by the electric source 104 and the application time thereof are set constant, the threshold thus determined may be stored in advance.

As has thus been described, according to the plasma liquid treatment device of the embodiment, the oxidizing power of the remaining plasma liquid can be easily and safely decreased. That is, when general water, purified water, water having a reducing power, or the like is simply mixed with the plasma liquid, the oxidizing power thereof can be decreased. In addition, since a plasma liquid having an oxidizing power is produced by generation of plasma, a plasma liquid having a high oxidizing power can be produced from water as a raw material without using a special chemical reagent.

In addition, in the above embodiment, although the oral cavity washing device has been primarily described as the plasma liquid treatment device, the plasma liquid treatment device may also be used for applications other than the oral cavity washing. For example, the plasma liquid treatment device of this embodiment may also be used, for example, for sterilization of medical devices, floors of bath rooms, drain ports, and window glasses.

In addition, the mixing of the plasma liquid and the water may be performed not only by ejection but also by mixing in a water bath.

In addition, in each embodiment described above, the constituent elements each may be formed using an exclusive hardware or may be realized by performing a software program suitable for each constituent element. The constituent elements each may be realized in such a way that a program execution portion, such as a CPU or a processor, reads and executes a software program stored in a storage medium, such as a hard disc or a semiconductor memory. In the present disclosure, a software which realizes the plasma liquid treatment device, the oral cavity washing device, and the like of the above embodiments enables a computer to implement the plasma liquid treatment method shown in FIG. 2.

Although the plasma liquid treatment device, the plasma liquid treatment method, and the oral cavity washing device according to at least one aspect of the present disclosure have thus been described in accordance with the embodiments, the present disclosure is not limited thereto. As long as being within the scope of the present disclosure, devices and methods each variously changed and/or modified by a person skilled in the art and devices and methods formed in combination of the constituent elements according to the embodiments different from each other may also be included in the range of the at least one aspect described above.

The plasma liquid treatment method according to the present disclosure may be used, for example, for oral cavity washing devices, sterilization of medical devices, floor washing of bath rooms, and washing of drain ports.

What is claimed is:

1. A method comprising:
   bringing a plasma-treated liquid having an oxidizing power into contact with an object in an area; and
   delivering water to the area from an external source to mix the water and the plasma-treated liquid which remains in the area after the plasma-treated liquid is brought into contact with the object,
   wherein the water is purified water or any water having a weaker oxidizing power as compared to that of the plasma-treated liquid.

2. A method comprising:
   bringing a plasma-treated liquid having an oxidizing power into contact with an object in an area; and
   mixing water and the plasma-treated liquid which remains in the area after the plasma-treated liquid is brought into contact with the object,
   wherein the plasma-treated liquid is ejected from an ejector controlled by a control circuit, to be brought into contact with the object;
   after the plasma-treated liquid is brought into contact with the object, the water is ejected from the ejector controlled by the control circuit, to be mixed with the plasma-treated liquid in the area, and
   the water is purified water or any water having a weaker oxidizing power as compared to that of the plasma-treated liquid.

3. The method according to claim 2, wherein after the ejector ejects the plasma-treated liquid, the control circuit controls the ejector to eject the water in accordance with a user operation received by an input circuit.

4. The method according to claim 2, wherein after a predetermined time passes from the start of ejection of the plasma-treated liquid, the ejector ejects the water.

5. The method according to claim 1, wherein the object is a portion to be sterilized in an oral cavity.

6. The method according to claim 2, wherein the object is a portion to be sterilized in an oral cavity.

7. The method according to claim 3, wherein the object is a portion to be sterilized in an oral cavity.

8. The method according to claim 4, wherein the object is a portion to be sterilized in an oral cavity.

* * * * *